United States Patent
Zook et al.

(10) Patent No.: US 7,459,458 B2
(45) Date of Patent: *Dec. 2, 2008

(54) POLYMORPH OF N-METHYL-N-(3-{3-[2-THIENYLCARBONYL]-PYRAZOL-[1,5-α]-PYRIMIDIN-7-YL}PHENYL)ACETAMIDE AND COMPOSITIONS AND METHODS RELATED THERETO

(75) Inventors: Scott E. Zook, San Diego, CA (US); Donald Hettinger, San Diego, CA (US); Henry R. DuBois, III, Catskill, NY (US)

(73) Assignee: Neurocrine Biosciences, Inc., San Diego, CA (US)

( * ) Notice: Subject to any disclaimer, the term of this patent is extended or adjusted under 35 U.S.C. 154(b) by 279 days.

This patent is subject to a terminal disclaimer.

(21) Appl. No.: 11/013,308

(22) Filed: Dec. 15, 2004

(65) Prior Publication Data

US 2005/0153988 A1    Jul. 14, 2005

Related U.S. Application Data

(63) Continuation of application No. 10/648,812, filed on Aug. 26, 2003, now Pat. No. 6,903,106.

(60) Provisional application No. 60/406,072, filed on Aug. 26, 2002.

(51) Int. Cl.
  *C07D 487/04*    (2006.01)
  *A61K 31/519*    (2006.01)
  *A61P 21/02*    (2006.01)
  *A61P 25/20*    (2006.01)
  *A61P 25/22*    (2006.01)

(52) U.S. Cl. .................... 514/259.3; 544/281

(58) Field of Classification Search ................ 544/281; 514/259.3

See application file for complete search history.

(56) References Cited

U.S. PATENT DOCUMENTS

| 6,384,221 B1 | 5/2002 | Thiele et al. ................ 544/281 |
| 6,399,621 B1 | 6/2002 | Dusza et al. ................ 514/258 |
| 6,472,528 B1 | 10/2002 | Gross et al. ................ 544/281 |
| 6,485,746 B1 | 11/2002 | Campbell et al. ........... 424/468 |
| 6,544,999 B2 | 4/2003 | Thiele et al. ............. 514/259.3 |
| 2002/0107256 A1 | 8/2002 | Thiele et al. ............. 514/262.1 |

FOREIGN PATENT DOCUMENTS

EA    004706    6/2004

*Primary Examiner*—James Wilson
*Assistant Examiner*—Susanna Moore
(74) *Attorney, Agent, or Firm*—Seed IP Law Group PLLC

(57) ABSTRACT

Polymorph Form III of N-methyl-N-(3-{3-[2-thienylcarbonyl]-pyrazol-[1,5-α]-pyrimidin-7-yl}phenyl)acetamide, and use thereof as a sedative-hypnotic, anxiolytic, anticonvulsant, and/or skeletal muscle relaxant agent. Related compositions and methods are also disclosed, particularly with regard to treatment of insomnia.

2 Claims, 3 Drawing Sheets

POLYMORPH OF N-METHYL-N-(3-{2-THIENYLCARBONYL]-PYRAZOL-[1,5-α]-PYRIMIDIN-7-YL}PHENYL)ACETAMIDE AND COMPOSITIONS AND METHODS RELATED THERETO

CROSS-REFERENCES TO RELATED APPLICATIONS

This application is a continuation of U.S. application Ser. No. 10/648,812 filed Aug. 26, 2003 (U.S. Pat. No. 6,903,106), which claims the benefit of U.S. Provisional Application No. 60/406,072 filed Aug. 26, 2002, both of which are hereby incorporated by reference in their entireties.

BACKGROUND OF THE INVENTION

1. Field of the Invention

This invention is generally directed to a novel polymorph of N-methyl-N-(3-{3-[2-thienylcarbonyl]-pyrazol-[1,5-α]-pyrimidin-7-yl}phenyl)acetamide which has activity over a wide range of indications, and is particularly useful for the treatment of insomnia, and to related processes, compositions and methods.

2. Description of the Related Art

The term "insomnia" is used to describe all conditions related to the perception of inadequate or non-restful sleep by the patient (Dement, *International Pharmacopsychiatry* 17:3-38, 1982). If left untreated, insomnia may result in disturbances in metabolism and overall body function including reduced productivity and significant changes in mood, behavior and psychomotor function, and a higher incidence of morbidity and mortality.

Traditionally, the management of insomnia includes treatment and/or mitigation of the etiological factors, improving sleep hygiene and the administration of hypnotic agents. The early hypnotic agents, such as barbiturates, while effective, elicited a spectrum of unwanted side effects and longer-term complications. For example, barbiturates have the potential to result in lethargy, confusion, depression and a variety of other residual effects many hours post dosing, as well as having a potential for being highly addictive.

During the 1980's, the pharmaceutical treatment of insomnia shifted away from barbiturates and other CNS depressants toward the benzodiazepine class of sedative-hypnotics. This class of sedative-hypnotic agents showed substantial effectiveness in producing a calming effect which results in sleep-like states in man and animals (Gee et al., Drugs in Central Nervous Systems, Horwell (ed.), New York, Marcel Dekker, Inc., 1985, p. 123-147) and had a greater safety margin than prior hypnotics, barbiturates or chloral hydrate (Cook and Sepinwall, Mechanism of Action of Benzodiazepines, Costa and Greengard (eds.), New York, Raven Press, 1975, p. 1-28). As with barbiturates, however, many benzodiazepines also possess side effects that limit their usefulness in certain patient populations. These problems include synergy with other CNS depressants (especially alcohol), the development of tolerance upon repeat dosing, rebound insomnia following discontinuation of dosing, hangover effects the next day, and impairment of psychomotor performance.

More recently, a new class of agents has undergone development. These agents are non-benzodiazepine compounds, which bind selectively to a specific receptor subtype of the benzodiazepine receptor. This receptor selectivity is thought to be the mechanism by which these compounds are able to exert a robust hypnotic effect, while also demonstrating an improved safety profile relative to the non-selective, benzodiazepine class of agents. The first of these agents to be approved by the United States Food and Drug Administration (FDA) for marketing in the United States was Ambien (zolpidem tartrate), which is based on the imidazopyridine backbone (see U.S. Pat. Nos. 4,382,938 and 4,460,592). In addition to Ambien, another compound known as Sonata (zaleplon), which is a pyrazolopyrimidine-based compound, has received FDA approval (see U.S. Pat. No. 4,626,538). Other non-benzodiazepine compounds and/or methods for making or using the same have also been reported (see, e.g., U.S. Pat. Nos. 4,794,185, 4,808,594, 4,847,256, 5,714,607, 4,654,347; 5,891,891).

While significant advances have been made in this field, there is still a need in the art for compounds that are effective as sedative or hypnotic agents generally, particularly in the context of treating insomnia. One such compound is N-methyl-N-(3-{3-[2-thienylcarbonyl]-pyrazol-[1,5-α]-pyrimidin-7-yl}phenyl)acetamide (referred to herein as "Compound 1"). Compound 1 is disclosed in U.S. Pat. No. 6,399,621 and has the following chemical structure:

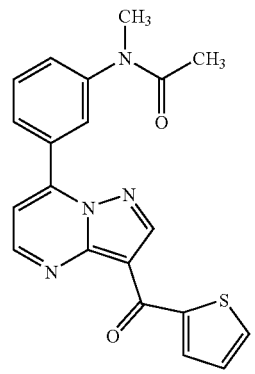

Compound 1

In addition, U.S. Pat. Nos. 6,384,221 and 6,544,999 are directed to polymorph Form I and Form II of Compound 1, while U.S. Patent Nos. 6,472,528 and 6,485,746 are directed to synthesis and controlled release, respectively, of Compound 1.

While Compound 1 has proven particularly promising for the treatment of insomnia, improved forms of this compound are desired, particularly with regard to enhanced solubility, oral bioavailability, ability to be readily formulated, ease of synthesis, and/or physical stability. The present invention fulfills one or more of these needs and provides further related advantages.

BRIEF SUMMARY OF THE INVENTION

The present invention is generally directed to a novel polymorphic form of Compound 1, referred to herein as "polymorph Form III". Polymorph Form III exhibits a predominant endotherm peak at about 191° C. (as measured by a TA 2920 Modulated Differential Scanning Calorimeter (DSC) at a scan rate of 10° C. per minute). Polymorph Form III also exhibits an X-ray Powder Diffraction pattern with characteristic peaks (expressed in degrees 2θ (+/−0.2° θ) at one or more of the following positions: 10.2, 13.3, 18.9, 20.7, 22.2, 28.1 and 30.8. More specifically, such characteristic peaks are at 18.9 and 28.1, and further at 10.2, and further at 13.3, 20.7, 22.2 and 30.8.

Polymorph Form III has utility over a wide range of applications, including utility as a sedative and/or hypnotic agent generally and, more specifically, for the treatment of insomnia. Thus, in another embodiment, methods are disclosed for treating various conditions, including insomnia, by administering an effective amount of polymorph Form III to an animal or subject in need thereof (referred to herein as a "patient"), and typically to a warm-blooded animal (including a human).

In one embodiment, polymorph Form III is substantially pure—that is, containing less than 2% by weight total impurities, less than about 1% by weight water, and less than 0.5% by weight residual organic solvent; or, in a more specifically embodiment, less than 1% by weight total impurities, less than about 0.75% by weight water, and less than 0.4% by weight residual organic solvent.

In another embodiment, Compound 1 is in the form of a composition or mixture of polymorph Form III along with one or more other crystalline, solvate, amorphous, or other forms of Compound 1. For example, such a composition may comprise polymorph Form III along with one or more other polymorphic forms of Compound 1, such as polymorph Form I and/or Form II. More specifically, the composition may comprise from trace amounts up to 100% polymorph Form III, or any amount in between—for example, the composition may comprise less than 0.1%, 0.5%, 1%, 2%, 5%, 10%, 20%, 30%, 40% or 50% by weight of polymorph Form III based on the total amount of Compound 1 in the composition. Alternatively, the composition may comprise at least 50%, 60%, 70%, 80%, 90%, 95%, 97%, 98%, 99%, 99.5% or 99.9% by weight of polymorph Form III based on the total amount of Compound 1 in the composition.

Prior to administration, and in further embodiment, polymorph Form III may be formulated as a pharmaceutical composition that contains an effective dosage amount of polymorph Form III in combination with one (or more) pharmaceutically acceptable carrier(s). Such compositions may assume a variety of forms, including pills, tablets and capsules for oral administration.

In still another embodiment, the pharmaceutical composition comprises an effective dosage amount of Compound 1, wherein Compound 1 comprises at least a certain percentage of polymorph Form III (based on the total amount of Compound 1 present in the composition—that is, the total amount of Compound 1 being 100%). In other words, at least a certain percentage of Compound 1 present within the pharmaceutical composition exists as polymorph Form III, with the remainder of Compound 1 being in a different form, including (but not limited to) polymorph Form I, polymorph Form II, or any other crystalline, solvate or amorphous form(s).

In yet a further embodiment, this invention provides processes for making polymorph Form III. For example, polymorph Form III may be made by (a) providing a heated crystallization solvent comprising Compound 1, (b) adding water and a nucleating agent (such as carbon or crystals of polymorph Form III) thereto in amounts sufficient to induce crystallization of polymorph Form III, and (c) collecting crystallized polymorph Form III. Optionally, the crystallization solvent can be cooled after step (b). In an alternative embodiment, polymorph Form III may be made by (a) providing a heated crystallization solvent comprising Compound 1, (b) adding the heated crystallization solvent to a co-solvent or mixture of co-solvents, (c) adding a nucleating agent thereto in amounts sufficient to induce crystallization of polymorph Form III, and (d) collecting crystallized polymorph Form III. Further, polymorph Form III made according to one or more of the processes of this invention is also disclosed.

These and other aspects of this invention will be apparent upon reference to the following detailed description and attached figures. To that end, certain patent and other documents are cited herein to more specifically set forth various aspects of this invention. Each of these documents is hereby incorporated by reference in its entirety.

DETAILED DESCRIPTION OF THE INVENTION

As mentioned above, the present invention is generally directed to a novel polymorphic form of Compound 1, referred to herein as "polymorph Form III", as well as to compositions containing the same. Also disclosed are methods relating to the use of polymorph Form III by administration to a patient in need of the same, and to processes for making polymorph Form III.

Solids exist in either amorphous or crystalline forms. In the case of crystalline forms, molecules are positioned in 3-dimensional lattice sites. When a compound recrystallizes from a solution or slurry, it may crystallize with different spatial lattice arrangements, a property referred to as "polymorphism," with the different crystal forms individually being referred to as a "polymorph". Different polymorphic forms of a given substance may differ from each other with respect to one or more physical properties, such as solubility and dissociation, true density, crystal shape, compaction behavior, flow properties, and/or solid state stability. In the case of a chemical substance that exists in two (or more) polymorphic forms, the unstable forms generally convert to the more thermodynamically stable forms at a given temperature after a sufficient period of time. When this transformation is not rapid, the thermodynamically unstable form is referred to as the "metastable" form. In general, the stable form exhibits the highest melting point, the lowest solubility, and the maximum chemical stability. However, the metastable form may exhibit sufficient chemical and physical stability under normal storage conditions to permit its use in a commercial form. In this case, the metastable form, although less stable, may exhibit properties desirable over those of the stable form, such as enhanced solubility or better oral bioavailability.

In the case of Compound 1, two polymorphic forms (i.e., Form I and Form II) have previously been reported (see U.S. Pat. Nos. 6,384,221 and 6,544,999). Compound 1 is presently undergoing clinical trials for treatment of insomnia. In anticipation of potential large-scale production, significant effort has been directed to the commercial-scale production of Compound 1. During one such production run, an impurity was discovered within the end product. In an effort to remove the impurity, carbon was added, followed by recrystallization. As a result of this subsequent work up, it was surprisingly discovered that a new polymorph (i.e., polymorph Form III) was obtained. While not intending to be limited by theory, it is believed that the added carbon served as a nucleation site for formation of polymorph Form III.

Figure 1:
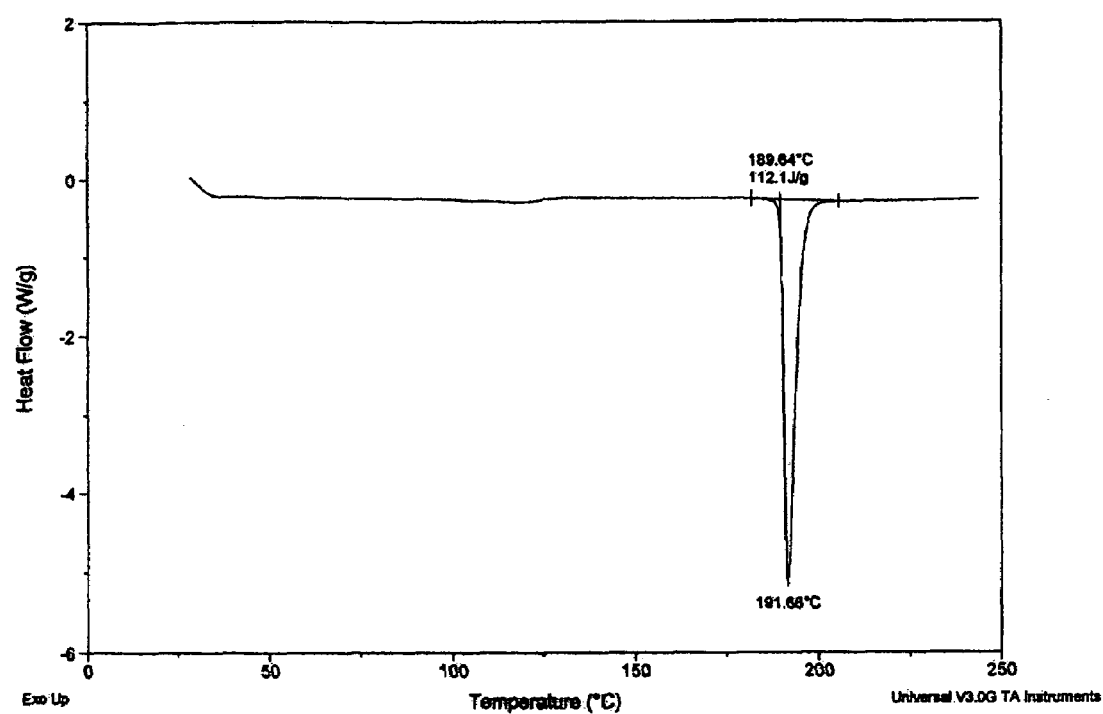
FIG. 1 is a Differential Scanning Calorimetry (DSC) thermogram of polymorph Form III.

The novel and surprising polymorph of this invention, polymorph Form III, may be characterized by, for example, melting point and/or X-Ray powder diffraction spectrometry. As shown in FIG. 1, polymorph Form III exhibits a predominant endotherm peak at about 191° C. as measured by a TA 2920 (TA Instruments, New Castle, Del.) Modulated Differential Scanning Calorimeter (DSC) at a scan rate of 10° C. per minute with an Indium standard. As used herein, the term "about 191° C." means a range of 190 to 192.5° C. In this regard, it should be understood that the endotherm measured by a particular differential scanning calorimeter is dependent upon a number of factors, including the rate of heating (i.e., scan rate), the calibration standard utilized, instrument calibration, relative humidity, and upon the chemical purity of the sample being tested. Thus, an endotherm as measured by DSC on the instrument identified above may vary by as much as ±1° C. or even ±1½° C. Accordingly, the term "about 191° C." is intended to encompass such instrument variations.

Figure 2:
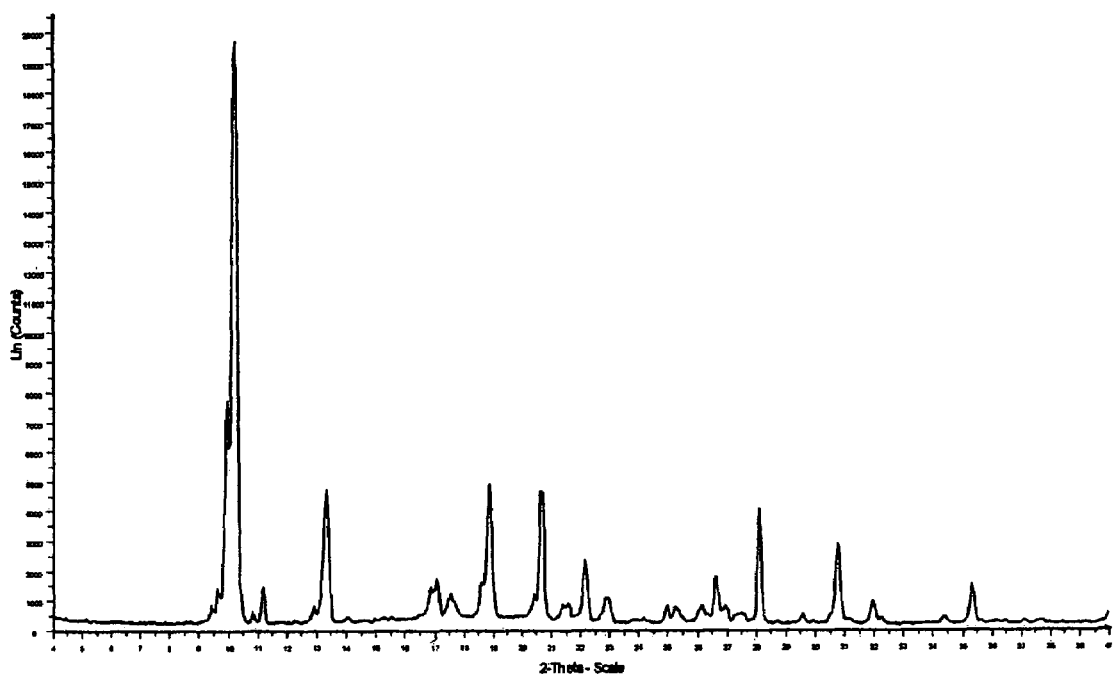
FIG. 2 is an X-ray powder diffraction spectrum of polymorph Form III.

The X-Ray powder diffraction spectrum for polymorph Form III is presented in FIG. 2, and is set forth in tabular form in Table 1 below. The X-Ray powder diffraction was measured by a Siemens D500 Automated Powder Diffractometer equipped with graphite monochromator and a Cu ($\lambda$=1.54 Angstrom) X-ray source operated at 50 kV, 40 mA. Two-theta calibration is performed using an NBS mica standard. The sample was analyzed using the following instrument parameters: measuring range=4-40° 2θ; step width=0.050°; and measuring time per step=1.2 sec.

TABLE 1

X-Ray Powder Diffraction Spectral Lines

| d value | 2-θ° | Intensity | Intensity % |
|---|---|---|---|
| 9.15587 | 9.652 | 1388 | 7.0 |
| 8.91589 | 9.912 | 7718 | 39.1 |
| 8.65670 | 10.210 | 19744 | 100.0 |
| 8.16181 | 10.831 | 572 | 2.9 |
| 7.88947 | 11.206 | 1398 | 7.1 |
| 6.85166 | 12.910 | 765 | 3.9 |
| 6.64840 | 13.306 | 4690 | 23.8 |
| 6.29329 | 14.061 | 396 | 2.0 |
| 5.24469 | 16.891 | 1398 | 7.1 |
| 5.19705 | 17.047 | 1731 | 8.8 |
| 5.05094 | 17.544 | 1170 | 5.9 |
| 4.76647 | 18.600 | 1567 | 7.9 |
| 4.69634 | 18.880 | 4865 | 24.6 |
| 4.34978 | 20.400 | 1131 | 5.7 |
| 4.29694 | 20.654 | 4611 | 23.4 |
| 4.12546 | 21.522 | 758 | 3.8 |
| 4.00186 | 22.195 | 2281 | 11.6 |
| 3.87889 | 22.908 | 1046 | 5.3 |
| 3.72796 | 23.849 | 321 | 1.6 |
| 3.56593 | 24.950 | 752 | 3.8 |
| 3.51637 | 25.307 | 716 | 3.6 |
| 3.40208 | 26.172 | 781 | 4.0 |
| 3.34446 | 26.631 | 1738 | 8.8 |
| 3.30597 | 26.947 | 764 | 3.9 |
| 3.23885 | 27.516 | 544 | 2.8 |
| 3.17029 | 28.124 | 4022 | 20.4 |
| 3.01819 | 29.572 | 480 | 2.4 |
| 2.97878 | 29.973 | 264 | 1.3 |
| 2.89811 | 30.827 | 2802 | 14.2 |
| 2.79651 | 31.977 | 890 | 4.5 |
| 2.77443 | 32.238 | 354 | 1.8 |
| 2.60380 | 34.415 | 407 | 2.1 |
| 2.53630 | 35.360 | 1434 | 7.3 |
| 2.41973 | 37.124 | 262 | 1.3 |
| 2.38437 | 37.695 | 253 | 1.3 |

The crystal structure of polymorph Form III was determined by single crystal X-ray diffraction analysis. A colorless plate of polymorph Form III having dimensions of 0.30×0.20×0.13 mm was mounted on a glass fiber in random orientation. Preliminary examination and data collection were performed with Mo K$_\alpha$ radiation ($\lambda$=0.71073 Å) on a Nonius KappaCCD diffractometer. Data relating to the single crystal X-ray crystallography of polymorph Form III is presented in the following Tables 2-6.

TABLE 2

Crystal Parameters

| Space Group | P2$_1$/n |
|---|---|
| a, Å | 9.5887(3) |
| b, Å | 10.3985(4) |
| c, Å | 17.5807(7) |
| α | 90 |
| β | 96.8044(14) |
| γ | 90 |
| Z (molecules/unit cell) | 4 |
| Calculated Density (g/cm) | 1.436 |
| Temperature (K.) | 150 |

TABLE 3

Positional Parameters and Their Estimated Standard Deviations

| Atom | x | y | z | U(Å$^2$) |
|---|---|---|---|---|
| S(1) | 0.46180(7) | −0.27982(8) | 0.14578(4) | 0.0384(2) |
| O(6) | 0.62938(19) | −0.0547(2) | 0.18402(10) | 0.0382(6) |
| O(122) | 0.8323(3) | 0.2180(3) | −0.36178(12) | 0.0643(8) |
| N(8) | 0.7964(2) | 0.1011(2) | 0.09047(13) | 0.0405(7) |
| N(9) | 0.8076(2) | 0.1723(2) | 0.15438(12) | 0.0317(6) |
| N(14) | 0.8428(2) | 0.0463(2) | −0.03115(11) | 0.0286(6) |
| N(12A) | 0.9717(5) | 0.2278(5) | −0.2546(3) | 0.0282(12) |
| N(12B) | 0.9122(5) | 0.3116(5) | −0.2521(3) | 0.0319(14) |
| C(2) | 0.3830(3) | −0.3736(3) | 0.07383(18) | 0.0420(9) |
| C(3) | 0.4087(3) | −0.3309(3) | 0.00378(17) | 0.0391(8) |
| C(4) | 0.4960(3) | −0.2230(3) | 0.00787(16) | 0.0331(7) |
| C(5) | 0.5358(2) | −0.1829(3) | 0.08160(14) | 0.0294(7) |
| C(6) | 0.6305(2) | −0.0805(3) | 0.11554(13) | 0.0280(7) |
| C(7) | 0.7219(2) | −0.0121(2) | 0.06857(13) | 0.0264(7) |
| C(10) | 0.8880(3) | 0.2745(3) | 0.15515(15) | 0.0333(7) |
| C(11) | 0.9616(3) | 0.3131(3) | 0.09337(14) | 0.0311(7) |
| C(12) | 0.9484(2) | 0.2422(3) | 0.02666(14) | 0.0269(6) |
| C(13) | 0.8667(2) | 0.1337(2) | 0.02781(11) | 0.0154(5) |
| C(15) | 0.7574(3) | −0.0389(3) | −0.00555(14) | 0.0289(7) |
| C(121) | 1.0127(3) | 0.2801(2) | −0.04226(14) | 0.0272(7) |
| C(122) | 1.1408(2) | 0.3451(2) | −0.03341(14) | 0.0278(7) |
| C(123) | 1.2019(3) | 0.3852(3) | −0.09671(14) | 0.0292(7) |
| C(124) | 1.1380(3) | 0.3615(3) | −0.17015(16) | 0.0412(8) |
| C(125) | 1.0100(4) | 0.2988(4) | −0.17857(16) | 0.0614(11) |
| C(126) | 0.9462(3) | 0.2586(3) | −0.11575(16) | 0.0453(8) |
| C(12A) | 0.8662(6) | 0.2827(7) | −0.3016(3) | 0.0324(17) |
| C(12B) | 0.9236(7) | 0.2085(7) | −0.2969(4) | 0.0361(17) |
| C(13A) | 1.0305(3) | 0.1070(3) | −0.27368(17) | 0.0446(9) |
| C(13B) | 0.8135(3) | 0.4141(3) | −0.27623(17) | 0.0430(9) |
| H(2) | 0.328 | −0.447 | 0.082 | 0.050 |
| H(3) | 0.371 | −0.370 | −0.043 | 0.047 |
| H(4) | 0.525 | −0.182 | −0.036 | 0.040 |
| H(10) | 0.898 | 0.326 | 0.200 | 0.040 |
| H(11) | 1.020 | 0.387 | 0.098 | 0.037 |
| H(15) | 0.723 | −0.112 | −0.034 | 0.035 |
| H(122) | 1.186 | 0.362 | 0.016 | 0.033 |
| H(123) | 1.289 | 0.430 | −0.090 | 0.035 |
| H(124) | 1.181 | 0.388 | −0.214 | 0.049 |
| H(126) | 0.857 | 0.217 | −0.123 | 0.055 |

U$_{eq}$ = (⅓)Σ$_i$Σ$_j$ U$_{ij}$a$_i$*a$_j$*a$_i$·a$_j$
Hydrogens included in calculation of structure factors but not refined.

TABLE 4

Anisotropic Temperature Factor Coefficients

| Name | U(1, 1) | U(2, 2) | U(3, 3) | U(1, 2) | U(1, 3) | U(2, 3) |
|---|---|---|---|---|---|---|
| S(1) | 0.0396(4) | 0.0424(5) | 0.0333(4) | −0.0081(3) | 0.0048(3) | 0.0054(3) |
| O(6) | 0.0505(11) | 0.0416(12) | 0.0240(10) | −0.0064(9) | 0.0105(8) | −0.0006(8) |
| O(122) | 0.0705(15) | 0.096(2) | 0.0248(11) | −0.0246(14) | −0.0014(10) | −0.0111(12) |
| N(8) | 0.0482(14) | 0.0424(15) | 0.0313(13) | 0.0033(11) | 0.0067(10) | 0.0017(11) |
| N(9) | 0.0430(12) | 0.0308(13) | 0.0220(11) | 0.0035(10) | 0.0067(9) | −0.0032(9) |
| N(14) | 0.0346(11) | 0.0299(12) | 0.0215(10) | −0.0007(9) | 0.0039(8) | −0.0037(9) |
| N(12A) | 0.035(2) | 0.035(3) | 0.013(2) | 0.000(2) | −0.0042(19) | 0.0008(19) |
| N(12B) | 0.035(2) | 0.036(3) | 0.024(3) | 0.005(2) | 0.0010(19) | 0.006(2) |
| C(2) | 0.0354(14) | 0.0386(18) | 0.0512(19) | −0.0088(12) | 0.0014(12) | 0.0004(14) |
| C(3) | 0.0359(15) | 0.0408(18) | 0.0386(16) | −0.0010(12) | −0.0037(11) | −0.0033(13) |
| C(4) | 0.0315(13) | 0.0382(17) | 0.0288(14) | 0.0034(11) | −0.0002(10) | −0.0007(12) |
| C(5) | 0.0295(13) | 0.0312(15) | 0.0275(13) | 0.0042(10) | 0.0036(10) | 0.0036(11) |
| C(6) | 0.0314(13) | 0.0292(14) | 0.0233(13) | 0.0033(10) | 0.0030(9) | 0.0025(10) |
| C(7) | 0.0336(13) | 0.0252(14) | 0.0208(12) | 0.0038(10) | 0.0043(9) | 0.0018(10) |
| C(10) | 0.0452(15) | 0.0324(16) | 0.0228(13) | −0.0004(12) | 0.0061(11) | −0.0033(11) |
| C(11) | 0.0396(14) | 0.0300(14) | 0.0236(12) | −0.0006(11) | 0.0038(10) | −0.0019(11) |
| C(12) | 0.0291(12) | 0.0308(14) | 0.0208(12) | 0.0034(10) | 0.0029(9) | 0.0023(10) |
| C(13) | 0.0207(10) | 0.0169(11) | 0.0089(9) | 0.0014(8) | 0.0030(7) | −0.0004(8) |
| C(15) | 0.0358(13) | 0.0282(14) | 0.0227(12) | 0.0010(10) | 0.0031(9) | −0.0011(10) |
| C(121) | 0.0317(13) | 0.0290(15) | 0.0211(12) | 0.0031(10) | 0.0034(9) | 0.0017(10) |
| C(122) | 0.0331(13) | 0.0258(14) | 0.0237(12) | 0.0014(10) | −0.0005(9) | −0.0012(10) |
| C(123) | 0.0303(13) | 0.0273(14) | 0.0298(13) | −0.0024(10) | 0.0030(10) | 0.0004(11) |
| C(124) | 0.0424(15) | 0.056(2) | 0.0253(14) | −0.0174(13) | 0.0041(11) | 0.0038(13) |
| C(125) | 0.058(2) | 0.106(3) | 0.0183(15) | −0.043(2) | −0.0035(13) | 0.0069(16) |
| C(126) | 0.0371(15) | 0.074(2) | 0.0232(14) | −0.0218(14) | −0.0028(11) | 0.0084(13) |
| C(12A) | 0.029(3) | 0.049(4) | 0.019(3) | −0.001(3) | 0.002(2) | 0.004(3) |
| C(12B) | 0.038(3) | 0.047(4) | 0.024(3) | −0.001(3) | 0.006(3) | −0.001(3) |
| C(13A) | 0.0548(18) | 0.0415(18) | 0.0357(16) | 0.0079(13) | −0.0024(12) | −0.0088(13) |
| C(13B) | 0.0461(16) | 0.048(2) | 0.0341(15) | 0.0134(13) | 0.0017(12) | 0.0084(13) |

The form of the anisotropic temperature factor is: exp[−2π {h$^2$a*$^2$U(1, 1) + k$^2$b*$^2$U(2, 2) + l$^2$c*$^2$U(3, 3) + 2hka*b*U(1, 2) + 2hla*c*U(1, 3) + 2klb*c*U(2, 3)}], where a*, b*, and c* are reciprocal lattice constants.

TABLE 5

Bond Distances

| Atom 6 | Atom 2 | Distance |
|---|---|---|
| S(1) | C(2) | 1.702(3) |
| S(1) | C(5) | 1.727(3) |
| O(6) | C(6) | 1.235(3) |
| O(122) | C(12A) | 1.263(7) |
| O(122) | C(12B) | 1.357(8) |
| N(8) | N(9) | 1.339(3) |
| N(8) | C(13) | 1.400(3) |
| N(8) | C(7) | 1.406(3) |
| N(9) | C(10) | 1.312(4) |
| N(14) | C(15) | 1.321(3) |
| N(14) | C(13) | 1.377(3) |
| C(2) | C(3) | 1.359(4) |
| C(3) | C(4) | 1.396(4) |
| C(4) | C(5) | 1.372(4) |
| C(5) | C(6) | 1.478(4) |
| C(6) | C(7) | 1.460(3) |
| C(7) | C(15) | 1.413(3) |
| C(10) | C(11) | 1.421(4) |
| C(11) | C(12) | 1.378(4) |
| C(12) | C(13) | 1.375(3) |
| C(12) | C(121) | 1.477(3) |
| C(121) | C(126) | 1.390(4) |
| C(121) | C(122) | 1.394(3) |
| C(122) | C(123) | 1.382(3) |
| C(123) | C(124) | 1.384(4) |
| C(124) | C(125) | 1.383(4) |
| C(125) | C(126) | 1.389(4) |
| C(125) | N(12B) | 1.510(5) |
| C(125) | N(12A) | 1.533(6) |
| N(12A) | C(12A) | 1.355(7) |
| N(12A) | C(13A) | 1.432(6) |
| C(12A) | C(13B) | 1.540(8) |
| N(12B) | C(12B) | 1.343(8) |
| N(12B) | C(13B) | 1.454(5) |
| C(12B) | C(13A) | 1.494(8) |

Numbers in parentheses are estimated standard deviations in the least significant digits.

TABLE 6

Bond Angles

| Atom 1 | Atom 2 | Atom 3 | Angle | Atom 1 | Atom 2 | Atom 3 | Angle |
|---|---|---|---|---|---|---|---|
| C(2) | S(1) | C(5) | 91.67(14) | C(126) | C(121) | C(122) | 118.9(2) |
| C(12A) | O(122) | C(12B) | 42.2(4) | C(126) | C(121) | C(12) | 122.0(2) |
| N(9) | N(8) | C(13) | 121.9(2) | C(122) | C(121) | C(12) | 119.1(2) |
| N(9) | N(8) | C(7) | 132.9(2) | C(123) | C(122) | C(121) | 120.5(2) |

TABLE 6-continued

Bond Angles

| Atom 1 | Atom 2 | Atom 3 | Angle | Atom 1 | Atom 2 | Atom 3 | Angle |
|---|---|---|---|---|---|---|---|
| C(13) | N(8) | C(7) | 105.3(2) | C(122) | C(123) | C(124) | 121.0(2) |
| C(10) | N(9) | N(8) | 116.5(2) | C(125) | C(124) | C(123) | 118.2(3) |
| C(15) | N(14) | C(13) | 103.91(19) | C(124) | C(125) | C(126) | 121.7(3) |
| C(3) | C(2) | S(1) | 112.0(2) | C(124) | C(125) | N(12B) | 120.2(3) |
| C(2) | C(3) | C(4) | 112.8(3) | C(126) | C(125) | N(12B) | 114.9(3) |
| C(5) | C(4) | C(3) | 113.0(3) | C(124) | C(125) | N(12A) | 116.0(3) |
| C(4) | C(5) | C(6) | 133.6(2) | C(126) | C(125) | N(12A) | 117.8(3) |
| C(4) | C(5) | S(1) | 110.5(2) | N(12B) | C(125) | N(12A) | 40.2(2) |
| C(6) | C(5) | S(1) | 115.89(18) | C(125) | C(126) | C(121) | 119.6(3) |
| O(6) | C(6) | C(7) | 121.4(2) | C(12A) | N(12A) | C(13A) | 120.9(5) |
| O(6) | C(6) | C(5) | 118.3(2) | C(12A) | N(12A) | C(125) | 114.4(5) |
| C(7) | C(6) | C(5) | 120.3(2) | C(13A) | N(12A) | C(125) | 124.5(4) |
| N(8) | C(7) | C(15) | 104.4(2) | O(122) | C(12A) | N(12A) | 112.7(6) |
| N(8) | C(7) | C(6) | 124.9(2) | O(122) | C(12A) | C(13B) | 130.8(5) |
| C(15) | C(7) | C(6) | 130.7(2) | N(12A) | C(12A) | C(13B) | 116.4(5) |
| N(9) | C(10) | C(11) | 124.4(2) | C(12B) | N(12B) | C(13B) | 120.6(6) |
| C(12) | C(11) | C(10) | 119.7(3) | C(12B) | N(12B) | C(125) | 110.2(5) |
| C(13) | C(12) | C(11) | 114.9(2) | C(13B) | N(12B) | C(125) | 129.1(4) |
| C(13) | C(12) | C(121) | 121.7(2) | N(12B) | C(12B) | O(122) | 110.2(6) |
| C(11) | C(12) | C(121) | 123.4(2) | N(12B) | C(12B) | C(13A) | 120.3(6) |
| C(12) | C(13) | N(14) | 125.07(19) | O(122) | C(12B) | C(13A) | 129.5(5) |
| C(12) | C(13) | N(8) | 122.6(2) | N(12A) | C(13A) | C(12B) | 33.8(3) |
| N(14) | C(13) | N(8) | 112.3(2) | N(12B) | C(13B) | C(12A) | 37.9(3) |
| N(14) | C(15) | C(7) | 114.1(2) | | | | |

Numbers in parentheses are estimated standard deviations in the least significant digits.

Figure 3:
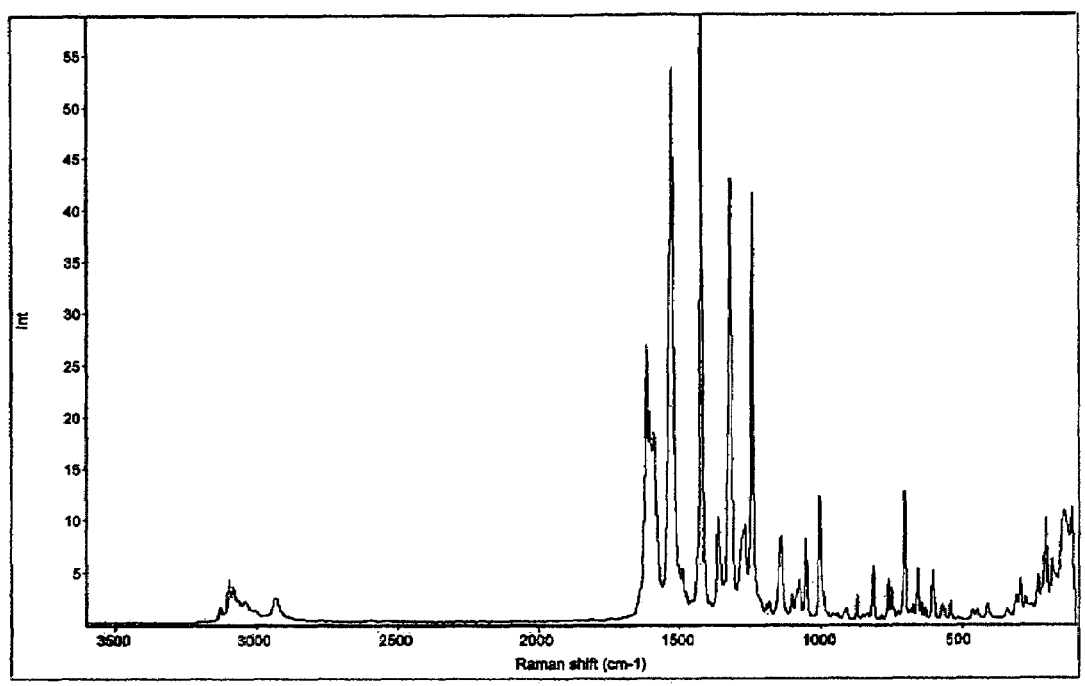
FIG. 3 is a Raman FT Infrared spectrum of polymorph Form III.

In addition, FIG. 3 shows the FT-Raman spectra of polymorph Form III as acquired on a Raman accessory module interfaced to a Magna 860® Fourier transform infrared (FT-IR) spectrophotometer (Thermo Nicolet). This module uses an excitation wavelength of 1064 nm and an indium gallium arsenide (InGaAs) detector. Approximately 0.5 W of Nd:YVO$_4$ laser power was used to irradiate the sample. The samples were prepared for analysis by placing the material in a glass tube and positioning the tube in a gold-coated tube holder in the accessory. A total of 256 sample scans were collected from 3600-100 cm$^{-1}$ at a spectral resolution of 4 cm$^{-1}$, using Happ-Genzel apodization. Wavelength calibration was performed using sulfur and cyclohexane.

Polymorph Form III may be prepared by crystallization from a crystallization solvent containing Compound 1. As used herein, the term "crystallization solvent" means a solvent or combination of solvents from which Compound 1 is preferentially crystallized as polymorph Form III. Representative crystallization solvents include polar solvents, nonpolar solvents, protic solvents and aprotic solvents, and more specifically include acetic acid, methylene chloride, acetone, methanol, ethanol, propanol, butanol, ethyl acetate, THF, DMF, diethyl ether, acetonitrile, toluene, water, and combinations thereof. In one embodiment, the crystallization solvent comprises acetic acid, to which water is gradually added.

Compound 1 may be introduced into the crystallization solvent in either a solid or liquid form. When added as a solid, Compound 1 may be in the form of a solid powder or any other solid form that aids its dissolution within the crystallization solvent. When added as a liquid, Compound 1 may first be dissolved in a co-solvent to yield a co-solvent solution, which is then combined with the crystallization solvent. The concentration of Compound 1 within the co-solvent solution may range from 0.1% by weight to the saturation point. This concentration will, of course, vary depending upon the temperature at which the co-solvent solution is held, with warmer temperatures generally allowing for the preparation of more concentrated solutions of Compound 1. In general, the co-solvent should aid in the dissolution of Compound 1, but not negatively interfere with the formation of polymorph Form III from the resulting crystallization solvent. Suitable co-solvents include the same solvents as identified above for the crystallization solvent. Further, the co-solvent and the crystallization solvent may be the same or different. For example, both the crystallization solvent and the co-solvent may be acetic acid, or they may be different solvents (or combinations thereof).

In one embodiment, the co-solvent solution containing Compound 1 is added to the crystallization solvent or, alternatively, the crystallization solvent is added to the co-solvent solution. In still another embodiment, the co-solvent solution may be at or above ambient temperature (e.g., heated), while the temperature of the crystallization solvent may be below (e.g., chilled), above (e.g., heated) or at ambient temperature. Alternatively, the co-solvent solution can undergo a solvent exchange and form a solution or heterogeneous mixture of the crystallization solvent and Compound 1. For example, Compound 1 may be dissolved in a first solvent, followed by addition to a second solvent, and then followed by removal of all or part of the first solvent (e.g., by distillation).

Crystallization of polymorph Form III may be achieved by addition of carbon or other nucleating agent to the crystallization solvent containing Compound 1. As used herein, a "nucleating agent" means a substance that aids in the formation of "nuclei" around which a crystal grows. Such nuclei may occur spontaneously in a supersaturated crystalline solvent and then will grow into larger crystals. Formation of the nuclei may also be induced by addition of a seed crystal or by the incidental or purposeful addition of some foreign solid matter such as dust or activated carbon. In a specific example (see Example 1 below), addition of a small amount of activated carbon to a heated solution of Compound 1 in acetic acid (60 mL) and water (70 mL), followed by subsequent cooling steps, yields polymorph Form III. The carbon may be added either before or after the addition of the water to result in formation of polymorph Form III.

Once obtained, crystals of polymorph Form III may be used as the nucleating agent or "seed" crystals for subsequent crystallizations of polymorph Form III from the crystallization solvent. In one embodiment, the crystallization solvent is formed by dissolving Compound 1 in hot acetone or other suitable crystallization solvent. The crystallization solvent is then seeded with crystals of polymorph Form III, cooled and filtered, resulting in polymorph Form III. In another embodiment, a crystallization solvent is formed by slurrying Compound 1 in acetone or other appropriate solvent. The crystallization solvent is then seeded with crystals of polymorph Form III and filtered, resulting in polymorph Form III. Such seeding with crystals of polymorph Form III may take place at any time during the slurrying process. Alternatively, seeding with crystals of polymorph Form III may take place prior to, or simultaneously with, addition of Compound 1 to the crystallization solvent.

Crystals of polymorph Form III may also be used as the nucleating agent or seed crystals in the conversion of a suspension or slurry of Compound 1 to produce polymorph Form III. Depending upon factors such as temperature, solvent and time, the resulting Compound 1 may be predominantly polymorph Form III, or may be polymorphic mixtures of Compound 1.

For purposes of administration to a patient, polymorph Form III may be formulated as a pharmaceutical composition. Such pharmaceutical compositions comprise polymorph Form III and one or more pharmaceutically acceptable carriers, wherein the polymorph is present in the composition in an amount that is effective to treat the condition of interest. Typically, the pharmaceutical compositions of the present invention include polymorph Form III in an amount ranging from 0.1 mg to 250 mg per dosage depending upon the route of administration, and more typically from 1 mg to 60 mg. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain—in addition to polymorph Form III—diluents, dispersing and surface-active agents, binders, lubricants, and/or delayed releases agents. One skilled in this art may further formulate the polymorph in an appropriate manner, and in accordance with accepted practices, such as those disclosed in Remington's Pharmaceutical Sciences, Gennaro, Ed., Mack Publishing Co., Easton, Pa. 1990 (incorporated herein by reference in its entirety).

In another embodiment, the invention provides a method for treating conditions that benefit from administration of agents that possess anxiolytic, anti-anoxic, sleep-inducing, hypnotic, anticonvulsant, and/or skeletal muscle relaxant properties. Such conditions include insomnia specifically, as well as sleep disorders generally and other neurological and psychiatric complaints, anxiety states, vigilance disorders, such as for combating behavioral disorders attributable to cerebral vascular damage and to the cerebral sclerosis encountered in geriatrics, epileptic vertigo attributable to cranial trauma, and for metabolic encephalopathies.

The methods of this invention include systemic administration of polymorph Form III, preferably in the form of a pharmaceutical composition. As used herein, systemic administration encompasses both oral and parenteral methods of administration. For oral administration, suitable pharmaceutical compositions include powders, granules, pills, tablets and capsules, as well as liquids, syrups, suspensions and emulsions. These compositions may also include flavorants, preservatives, suspending, thickening and emulsifying agents, and other pharmaceutically acceptable additives. For parental administration, the compounds of the present invention can be prepared in aqueous injection solutions that may contain buffers, antioxidants, bacteriostats and/or other additives commonly employed in such solutions.

The following examples are offered by way of illustration, not limitation.

EXAMPLE 1

Representative Synthesis of Polymorph Form III

Compound 1 (10 g) made according to the procedures of U.S. Pat. No. 6,399,621 (incorporated herein by reference) was dissolved in 60 mL of acetic acid. The solution was then filtered and heated to 70-75° C. Water (70 mL) and carbon (Darco G-60, 5 mg) were added to the heated solution, and the resulting solution was then cooled 5° C. every 30 minutes. At 55° C., crystallization began and the temperature was held steady for 30 minutes. The mixture was then cooled to 45-50° C. and 40 mL of water was added. The mixture was further cooled to 25° C. over a 1 hour period and the resulting solid was filtered and washed with 40 mL of water and dried to yield 9 g of polymorph Form III as a yellow solid (see FIGS. 1 and 2 for characterization of Polymorph Form III by DSC and X-ray powder diffraction).

EXAMPLE 2

Representative Synthesis of Polymorph Form III

Compound 1 (10 g) made according to the procedure of U.S. Pat. No. 6,399,621 was dissolved in 60 mL of acetic acid. The solution was then filtered and heated to 70-75° C. Water (70 mL) was added to the heated solution. After cooling to 67° C., polymorph Form III seed crystals (as obtained by the procedure described in Example 1 above) were added and the mixture was cooled to 50° C. over 2 hours. 40 mL of water was added and the mixture was cooled to room temperature. The resulting solid was filtered and washed with 40 mL of water to yield 9 g of polymorph Form III as a yellow solid (DSC endotherm peak at 191.86° C.).

EXAMPLE 3

Representative Synthesis of Polymorph Form III

Compound 1 (10 g) was prepared according to the procedure of U.S. Pat. No. 6,399,621 and dissolved in 60 mL of acetic acid. The solution was then filtered and heated to 70-75° C. Water (70 mL) was added to the heated solution. After cooling to 52° C., polymorph Form III seed crystals (as obtained by the procedure described in Example 1) were added and the mixture was stirred for 30 minutes. The mixture was then cooled to 47° C. over 30 minutes followed by addition of 40 mL of water. Following cooling to room temperature, the resulting solid was filtered and washed with 40 mL of water to yield 9 g of polymorph Form III as a yellow solid (DSC endotherm peak at 191.68° C.).

EXAMPLE 4

Interconversion of Compound 1

Interconversion experiments were carried out to evaluate the thermodynamic stability of Compound 1 at room temperature. Three slurries were prepared by making saturated isopropanol solutions of Compound 1, filtering the solutions through 0.2 µm filters, and then adding an amount (in the form of crystals) of a polymorphic form of Compound 1. To the first slurry, equal amounts of both polymorph Form II and polymorph Form III (i.e., approximately 25 mg each) were added; to the second slurry, equal amounts of polymorph From I and polymorph Form III (i.e., approximately 25 mg each) were added; and to the third slurry, approximately 25 mg of polymorph Form III was added. The slurries were then agitated for 16 days. The resulting solids were collected by vacuum filtration, air-dried, and analyzed using XRPD. By the above technique, the first slurry seeded with polymorph Forms II and III yielded exclusively polymorph Form III. On the other hand, the second slurry seeded with polymorph Forms I and III yielded polymorph Form III as the predominant product, with only a minor amount of polymorph Form I. The third slurry seeded with polymorph Form III alone yielded exclusively polymorph Form III. These results indicate that Compound 1, when in a slurry form, will convert to polymorph Form III when seeded with crystals of the same, and under such conditions is the favored polymorph.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims.

We claim:

1. A method for inducing sedation in a patient in need thereof, comprising administering to the patient an effective amount of a composition comprising polymorph Form III of N-methyl-N-(3-{3-[2-thienylcarbonyl]-pyrazol-[1,5-α]-pyrimidin-7-yl}phenyl)acetamide in crystalline form in combination with a pharmaceutically acceptable carrier.

2. A method for inducing skeletal muscle relaxation in a patient in need thereof, comprising administering to the patient an effective amount of a composition comprising polymorph Form III of N-methyl-N-(3-{3-[2-thienylcarbonyl]-pyrazol-[1,5-α]-pyrimidin-7-yl}phenyl)acetamide in crystalline form in combination with a pharmaceutically acceptable carrier.

* * * * *